(12) United States Patent
Levine et al.

(10) Patent No.: US 8,361,519 B2
(45) Date of Patent: Jan. 29, 2013

(54) COMBINATION HERBAL PRODUCT TO BENEFIT RESPIRATORY TRACT IN PEOPLE EXPOSED TO SMOKE

(75) Inventors: Brian M. Levine, Coto de Caza, CA (US); William E. Berger, Coto de Caza, CA (US)

(73) Assignee: Aadvantics Pharmaceuticals, Inc., Coto de Caza, CA (US)

( * ) Notice: Subject to any disclaimer, the term of this patent is extended or adjusted under 35 U.S.C. 154(b) by 0 days.

(21) Appl. No.: 13/297,534

(22) Filed: Nov. 16, 2011

(65) Prior Publication Data

US 2012/0128801 A1 May 24, 2012

Related U.S. Application Data

(60) Provisional application No. 61/415,106, filed on Nov. 18, 2010.

(51) Int. Cl.
- *A01N 65/00* (2009.01)
- *A61P 11/00* (2006.01)
- *A61P 11/14* (2006.01)
- *A61P 29/00* (2006.01)
- *A61P 39/06* (2006.01)

(52) U.S. Cl. ........ 424/725; 424/745; 424/735; 424/441; 514/850; 514/855

(58) Field of Classification Search .................. None
See application file for complete search history.

(56) References Cited

U.S. PATENT DOCUMENTS

| | | | |
|---|---|---|---|
| 3,061,517 A | | 10/1962 | Lewis et al. |
| 4,029,797 A | * | 6/1977 | Bianculli |
| 4,619,934 A | | 10/1986 | Sunshine et al. |
| 4,840,949 A | | 6/1989 | Korbonits et al. |
| 5,681,577 A | | 10/1997 | Leech et al. |
| 6,037,358 A | | 3/2000 | Gordziel |
| 6,306,904 B1 | | 10/2001 | Gordziel |
| 6,319,513 B1 | | 11/2001 | Dobrozsi et al. |
| 6,348,470 B1 | | 2/2002 | Korbonits et al. |
| 6,362,197 B1 | | 3/2002 | Page et al. |
| 6,417,206 B1 | | 7/2002 | Leflein et al. |
| 6,509,492 B1 | | 1/2003 | Venkataraman et al. |
| 6,638,521 B2 | | 10/2003 | Dobrozsi et al. |
| 6,670,370 B1 | | 12/2003 | Chopdekar et al. |
| 6,790,980 B1 | | 9/2004 | Venkataraman et al. |
| 6,979,689 B2 | | 12/2005 | Gonzales et al. |
| 7,914,828 B2 | * | 3/2011 | Levine et al. |
| 2002/0009478 A1 | | 1/2002 | Dobrozsi et al. |
| 2002/0082307 A1 | | 6/2002 | Dobrozsi et al. |
| 2003/0077321 A1 | | 4/2003 | Kiel et al. |
| 2003/0118613 A1 | | 6/2003 | Dobrozsi et al. |
| 2004/0029864 A1 | | 2/2004 | Macmillan |
| 2004/0033961 A1 | | 2/2004 | Gremminger et al. |
| 2005/0020509 A1 | | 1/2005 | Kiel et al. |

* cited by examiner

*Primary Examiner* — Michael C. Flood

(74) *Attorney, Agent, or Firm* — Stetina Brunda Garred & Brucker

(57) ABSTRACT

An herbal composition for providing a beneficial effect to the respiratory tract. The composition includes Thyme Leaf, Wild Cherry Bark, Cocoa Extract, Mullein Leaf Extract, and *Boswellia Serrata*. In particular, the composition may prevent or treat cough, specifically caused by exposure to smoke. Also described are methods of using the herbal composition.

10 Claims, 1 Drawing Sheet

| FREQUENCY OF COUGH EPISODES | Visit 1 | Visit 2 | Visit 3 | Visit 4 | Visit 5 |
|---|---|---|---|---|---|
| None | | | | | |
| Almost Never: 0-2 spells per day | | | | | |
| Little: 3-14 spells per day | | | | | |
| Somewhat: 15-30 spells per day | | | | | |
| Much: 31-40 spells per day | | | | | |
| Very Much: 40+ spells per day | | | | | |

| SEVERITY OF COUGH EPISODES | Visit 1 | Visit 2 | Visit 3 | Visit 4 | Visit 5 |
|---|---|---|---|---|---|
| Mild | | | | | |
| Moderate | | | | | |
| Severe | | | | | |
| Very Severe | | | | | |

COMBINATION HERBAL PRODUCT TO BENEFIT RESPIRATORY TRACT IN PEOPLE EXPOSED TO SMOKE

CROSS-REFERENCE TO RELATED APPLICATIONS

This application claims the benefit of U.S. Provisional Application No. 61/415,106, filed on Nov. 18, 2010, the teachings of which are expressly incorporated by reference.

STATEMENT RE: FEDERALLY SPONSORED RESEARCH/DEVELOPEMENT

Not Applicable

BACKGROUND

1. Field of the Invention

The present invention relates to a novel synergistic herbal composition for providing beneficial effects to the respiratory tract of a mammal. In particular, the herbal composition may be used for preventing and treating cough, specifically caused by exposure to smoke. The herbs in the present invention are a unique combination including, Thyme Leaf, Wild Cherry Bark, Cocoa Extract, Mullein Leaf Extract, and *Boswellia Serrata*.

2. Background of the Invention

Disorders of the respiratory tract, caused by post-nasal drip, sinus infections, gastrosoesophageal reflux (GERD), asthma, and medications, all can result in cough. However, there is no more specific and obvious cause of cough than smoke exposure. The act of coughing is a protective reflex. But, persistent cough is abnormal, and can dramatically affect one's quality of life, when it becomes excessive and/or profound. Coughing due to smoke exposure, even second hand exposure can cause substantial physical, as well as emotional harm. Millions of people, on a daily basis, smoke tobacco products, are exposed to second hand smoke, or are exposed to smoke cause by fires. Despite this fact, there is no commercially available product that has been proven to beneficially support the respiratory tract and, thus, reduce their tendency to cough.

It has been well documented that smoke exposure causes particle deposition, inflammatory changes, and excessive secretions in the entire respiratory tract as well as bronchospasms and decreased ciliary activity in the lower respiratory tract. These disturbances all can contribute to the severity of cough. In addition, it has been documented that only 25-40% of people who are exposed to smoke do, in fact, cough. It is believed that those people have overactive nicotine receptors found in the sensory nerve endings, located throughout the respiratory tract. It becomes obvious that to successfully alleviate cough, a combination product to treat each, and all of the respiratory tract disturbances, become imperative.

Herbal products, in the form of nutritional supplements have been used for centuries to treat medical disorders. Since a void exists for therapeutic products that actually work to support the respiratory tract, the use of herbal alternatives has gained greater attention. Furthermore, recent data has suggested that combinations of herbal supplements, such as has been used in traditional Chinese Medicine, can provide benefits to the respiratory tract. Allergic rhinitis and asthma, for example, have been shown to improve with this herbal combination approach.

Since there are a multitude of herbal products on the market, it becomes imperative to identify those products having a long history of safe use, as well as having had clinical studies that actually demonstrate effectiveness. It is believed that combinations of these herbal supplements can help reduce the tendency to cough by providing beneficial effects to the respiratory tract, altered by smoke inhalation.

BRIEF SUMMARY

The present invention encompasses a synergistic herbal combination, potentially in the form of a chewable tablet or liquid, and is comprised of five key ingredients that together support respiratory health. The five ingredients have been commercially available for health benefits over the past several years. However, they have never been used in specific combination. Each 2 oz liquid dose, or chewable tablet, contains the following ingredients: Thyme Leaf (*Thymus vulgaris*), Wild Cherry Bark (*Prunus serotina*), Cocoa Extract (*Theobroma cacao*), Mullein Leaf Extract (*Verbascum densiflorum*), and *Boswellia Serrata*. It is contemplated that one may use commercially available herbal products to produce the presently disclosed synergistic herbal combination product. In particular, one specific embodiment envisions an herbal composition for providing a beneficial effect to the respiratory tract of a mammal, including humans. The herbal composition may include the following as an active ingredient: Thyme Leaf, Wild Cherry Bark, Cocoa Extract, Mullein Leaf Extract, and *Boswellia Serrata*. The herbal composition may be used to prevent or treat cough caused by smoke. Notably this may be achieved by one or more of the following beneficial aspects of the composition: cough suppression, demulcent, anti-inflammatory effect, antispasmodic, antioxidant, expectorant action, and bronchospastic relief.

It is envisioned that the herbal composition of the present invention may be formulated and administered in various forms, including, but not limited to dietary supplements, chewable tablets, and liquid formulations. In particular, the herbal composition may include varied and numerous inactive ingredients known within the art to improve the formulation, delivery, preservation, appearance, and administration of the active ingredient.

Although the herbal composition is contemplated to be used in varying amounts of each herb, one particular embodiment utilizes a weight ratio of Thyme Leaf, Wild Cherry Bark, Cocoa Extract, Mullein Leaf Extract, and *Boswellia Serrata* about 1:3.75; 1; 1.875; 3:75. In particular, and for the average adult human, the herbal composition may be formulated in the following amounts: 40 mg. Thyme Leaf Extract, 50 mg. Wild Cherry Bark, 40 mg. Cocoa Extract, 75 mg. Mullein Leaf Extract, 150 mg. *Boswellia Serrata*. Alternatively, the herbal composition could be formulated in the following amounts 80 mg. Thyme Leaf Extract, 300 mg. Wild Cherry Bark, 80 mg. Cocoa Extract, 150 mg. Mullein Leaf Extract, 300 mg. *Boswellia Serrata*. In these instances, a patient could take two doses of the former to achieve the same results as a single dose of the latter.

It is believed that a preferred embodiment of the present invention would be within the following ranges: 25-600 mg. Thyme Leaf, 25-600 mg. Wild Cherry Bark, 25-600 mg. Cocoa Extract, 25-600 mg. Mullein Leaf Extract, 25-600 mg. *Boswellia Serrata*.

The present invention further contemplates a method of treating cough, caused by smoke, in a mammal by administering an effective amount of the herbal composition described herein to a mammal in need thereof. In particular, an adult human could receive beneficial effects by being administered, in chewable tablet or liquid form, the herbal composition of the present invention, twice or thrice daily.

BRIEF DESCRIPTION OF THE DRAWINGS

These and other features and advantages of the various embodiments disclosed herein will be better understood with respect to the following description and drawings, in which:

FIG. 1 shows a sample chart for objectively monitoring frequency and severity of cough episodes.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

One embodiment of the present invention encompasses a novel synergistic herbal composition that benefits the respiratory tract. In particular, the novel herbal composition of this embodiment is useful in preventing and/or treating cough caused by smoke.

The act of coughing is a complicated process. Disturbance of the respiratory tract can trigger neurohumoral consequences that, ultimately, may result in cough. The cough reflex is truly a protective mechanism. However, when stimulated by smoke, the cough frequency and severity can be greatly heightened, and dramatically affect one's quality of life.

Prior treatment outcomes for a large number of patients having chronic cough due to smoke inhalation remain dismal. There are several ways in which herbal ingredients may act to treat cough, e.g., 1) via central nervous system action; 2) via local anesthetic effect 3) as a demulcent (soothing effect); 4) as a surfactant; 5) as an expectorant; 6) as a mucolytic; 7) as a antispasmodic; 8) as an anti-inflammant; 9) as an antioxidant; 10) as an antihistamine; or 11) as a decongestant. It would, indeed, seem likely that combined effects provided by multiple herbal ingredients could have a greater chance of treatment success in a patient population in which no modality has previously worked.

There are many combination herbal cough preparations commercially available throughout the world. However, the novel herbal combination of the present invention represents the first time that a combination herbal cough product has undergone both subjective as well as objective outcome measurement in people chronically exposed to smoke.

Components of the Herbal Composition

The novel herbal composition of the present invention includes the following active ingredients: Thyme Leaf, Wild Cherry Bark, Cocoa Extract, Mullein Leaf Extract, and *Boswellia Serrata*. Each of the listed active ingredients will be discussed in greater detail below. Furthermore, along with the active ingredients, it is contemplated that additional inactive ingredients, such as but not limited to carriers, adjuvants, diluents, fillers, emulsifiers, preservatives, and flavoring agents, may be added to the composition to prepare the composition in a suitable form for administration to a patient, e.g., tablet form.

Thyme (*Thymus vulgaris*) is a leaf extract that contains volatile oils, such as thymol, as well as flavonoids (plant pigments). As a result, thyme commonly is used as an antitussive and antispasmodic. It also contains terpines that stimulate the cilia (fine hair-like structures in the lower respiratory tract) to beat and increase mucous movement to the upper respiratory tract (expectorant action). Furthermore, it has an anti-inflammatory effect, resulting in decreased nitric oxide production.

Wild Cherry Bark (*Prunus serotina*) is a tree bark extract that contains prunasin, a potent cough suppressant. It has also been reported to have an antioxidant effect. Wild Cherry Bark has, furthermore, been demonstrated to have a mild sedative effect, desirable during periods of illness.

Cocoa Extract (*Theobroma cacao*) contains tannins, purine alkaloids, flavonoids, and caffeine. The components of the cocoa extract produce antitussive, antispasmodic, as well as anti-inflammatory effects.

Mullein Leaf Extract (*Verbascum densiflorum*) contains mucilage, saponins, and flavonoids. It also has anti-inflammatory and expectorant action.

*Boswellia Serrata* is a tree resin gum that has significant anti-inflammatory effects. It has also been demonstrated to produce bronchial dilation.

All of the above listed compounds are known and available to those within the art. In the clinical trial below, the compounds were obtained from GMP Laboratories of Anaheim, Calif.

EXAMPLE 1

Components and Effective Ranges

The components and effective dose ranges of the herbs used in herbal composition of the present invention are shown in Table 1.

TABLE 1

| Effective Dose Range | |
|---|---|
| Ingredient | Weight (mg) |
| Thyme Leaf | 25-600 |
| Wild Cherry Bark | 25-600 |
| Cocoa Extract | 25-600 |
| *Mullein* Leaf Extract | 25-600 |
| *Boswellia Serrata* | 25-500 |

Table 2 shows a first example of a 2 oz liquid dose formulation of the present invention, wherein the 2 oz liquid dose also contains the inactive ingredients.

TABLE 2

| First Example, 2 oz Liquid Dose | |
|---|---|
| Ingredient | Weight (mg) |
| Thyme Leaf | 40 |
| Wild Cherry Bark | 150 |
| Cocoa Extract | 40 |
| *Mullein* Leaf Extract | 75 |
| *Boswellia Serrata* | 150 |

Table 3 shows a second example of a chewable tablet formulation of the present invention. In particular, the formulation of Table 3 is the formulation used in the clinical study described below.

TABLE 3

Second Example, One Chewable Tablet

| Ingredient | Weight (mg) |
|---|---|
| Thyme Leaf | 150 |
| Wild Cherry Bark | 150 |
| Cocoa Extract | 40 |
| *Mullein* Leaf Extract | 60 |
| *Boswellia Serrata* | 150 |

Suggested dosing for the described tablets to an average human patient would thus be 1-2 tablets, or a 2 oz liquid dose, 2-3 times a day.

EXAMPLE 2

Clinical Study

1. Patients

Eligible candidates were identified from a database of adult patients who had sought care at The Cough Center, in Laguna Hills, Calif. in 2009. A total of 5 patients (2 women and 3 men) with cough that persisted unabated for several years (chronic cough) were studied. All subjects shared a common history: 1) each had a 2 pack per day smoking history; 2) their cough profoundly diminished their quality of life; and 3) no medication(s) other than narcotic derivatives were ever able to alleviate their cough. The patients had previously undergone a complete evaluation and treatment program, following the guidelines established by The American College of Chest Physicians. All patients were provided with written information prior to obtaining consent.

2. Study Design

The subjects participated in a three week study. Patients with severe and chronic cough, and whom had smoked cigarettes for several years, were chosen. In this patient population, any improvement, even a small improvement, can be viewed as being statistically significant. Because the combination herbal product had such a unique taste, adequate placebo controls were difficult to devise. Regardless, it has been a well documented fact that placebo responses in chronic cough patients simply do not occur. This is possibly due to the prolonged duration of symptoms and multiple previous therapeutic trials. Therefore, patients with chronic cough serve as their own control.

Preceding the study, each patient underwent an initial office evaluation to rule out any recent or unrecognized cause of cough, other than smoking. All cough suppressants decongestants, antihistamines, anti-inflammatories, expectorants, and narcotics were eliminated prior to the study.

Each patient was required to take one chewable tablet of the combination herbal product as described in Table 3, twice daily. At the end of the three week period of treatment, another office evaluation was performed. Subjective, as well as objective measurement techniques, were then administered at each office visit to determine success of treatment.

Each tablet contained Thyme Leaf Extract (*Thymus Vulgaris*) 150 mg. Wild Cherry Bark (*Prunus serotina*) 150 mg. Cocoa Extract (*Theobroma Cacao*) 40 mg., Mullein Leaf Extract (*Verbascum Densiflorum*) 60 mg., and *Boswellia Serrata* 150 mg.

3. Clinical Evaluation

The goal of successful treatment was cough resolution or cough reduced to the extent that it was no longer dominating one's quality of life (QOL). The assessment of treatment success was based on the positive trends noted with both subjective and objective evaluation. At pre- and post-treatment evaluations, a subjective measurement was attained using the Leicester Cough-Specific QOL Questionnaire, as described in the article Development of a Symptom Specific Healthy Status for Patients with Chronic Cough; Leicester Cough Questionnaire (LCQ) by Birring et al., published in Thorax 2003; 58: 339-343. The questionnaire provides a validated and reproducible measure of the impact of chronic cough on activities of daily living. The subjects score the 19-item questionnaire based on physical, social, and psychological effects of cough. An objective system of cough monitoring was devised to assess both frequency and severity of coughing (FIG. 1). It should be noted that cough episodes or "epochs" were recorded rather than each individual cough. This system of evaluation became necessary because 1) a cough monitor for the many patients was impractical; 2) there is a wide difference of opinions as to what constitutes an individual "cough sound"; 3) the impact of coughing episodes seems to be recalled more accurately than each individual cough; and 4) the severity of coughing may have more of an impact than that of frequency of episodes. Each category of evaluation, frequency, severity, and Leicester QOL (LQOL) score was given equal weighting when treatment success was determined. For example, if frequency of episodes decreased 80-100%, severity diminished 75-100%, and LQOL score changed >2.6 points, then that individual would be categorized as being "improved". If frequency of episodes decreased 0-10%, severity diminished 0-15%, LQOL score changed <1.3 points, then that individual would be categorized as being "not improved". Individuals with values in between those two extremes were categorized as being "somewhat improved".

4. Statistical Analysis

Data for age and cough duration were expressed as median (range) values. Response rates were analyzed by paired T-tests. Group comparisons were performed using the Fisher two-tailed exact test. A value of $p<0.05$ was considered statistically significant.

5. Results

A total of 5 patients were initially enrolled in the study with a median (SD) age of 54 (10.2) years were studied. The median duration of cough was 5 years (60 months) with a range of 2 months to 60 years. Two of the five patients were female, three were male. Of the 5 patients, none had adverse side effects. All patients completed the three week study.

Upon evaluation, it was determined that 4 of the 5 patients studied (80%) demonstrated a statistically significant improvement in the frequency, severity, and subjective assessment of their quality of life, with the use of the combination herbal product. Of the 4 "improved" patients, 3 were "much improved" and 1 were "somewhat improved." Unfortunately, the cough for 1 patient was "not improved". The three patients that had marked improvement had immediate improvement within one hour of digestion of the chewable tables identified in Example 2.

6. Conclusion

The results of this study showed that this particular novel combination herbal product can make a significant difference in the cough management in many patients chronically exposed to smoke with which no other treatment, short of (or including) narcotics, was successful. Furthermore, it has been demonstrated that the novel combination herbal product can be tolerated well, causing no side effects. Of greatest importance, however, is the fact that the novel combination herbal product has been shown to make a statistically significant improvement in the quality of life in patients having persistent cough caused by exposure to smoke.

The above description is given by way of example, and not limitation. Given the above disclosure, one skilled in the art could devise variations that are within the scope and spirit of the invention disclosed herein, including varying the amounts of each herbal composition and including additional inactive ingredients to make the composition more suitable for administration to a patient. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An herbal composition for providing a beneficial effect to the respiratory tract of a mammal, comprising:
    an active ingredient consisting essentially of Thyme Leaf, Wild Cherry Bark, Cocoa Extract, Mullein Leaf Extract and *Boswellia Serrata*.

2. The herbal composition of claim 1, wherein the beneficial effect is the reduction or treatment of cough in mammals with chronic smoke exposure as a cause.

3. The herbal composition of claim 2, wherein the beneficial effect is at least one from the group consisting of cough suppression, demulcent, anti-inflammatory effect, antispasmodic, antioxidant, expectorant action, and bronchospastic relief.

4. The herbal composition of claim 1, wherein the mammal is a human.

5. The herbal composition of claim 1, wherein the herbal composition is formulated as a dietary supplement.

6. The herbal composition of claim 1, wherein the herbal composition is formulated as a chewable tablet or liquid.

7. The herbal composition of claim 1, wherein the Thyme Leaf, Wild Cherry Bark, Cocoa Extract, Mullein Leaf Extract, and *Boswellia Serrata* are at a weight ratio of about 1; 3.75; 1; 1.875; 3.75.

8. The herbal composition of claim 7, wherein the active ingredient consists essentially of 40 mg. Thyme Leaf, 150 mg. Wild Cherry Bark, 40 mg. Cocoa Extract, 75 mg. Mullein Leaf Extract, and 150 mg. *Boswellia Serrata*.

9. The herbal composition of claim 7, wherein the active ingredient consists essentially of 80 mg. Thyme Leaf, 300 mg. Wild Cherry Bark, 80 mg. Cocoa Extract, 150 mg. Mullein Leaf Extract, and 300 mg. *Boswellia Serrata*.

10. The herbal composition of claim 1, wherein the active ingredient consists essentially of 25-600 mg. Thyme Leaf, 25-600 mg. Wild Cherry Bark, 25-600 mg. Cocoa Extract, 25-600 mg. Mullein Leaf Extract, 25-600 mg. *Boswellia Serrata*.

\* \* \* \* \*